United States Patent
Kodama et al.

(10) Patent No.: US 10,809,239 B2
(45) Date of Patent: Oct. 20, 2020

(54) GAS SENSOR

(71) Applicant: DENSO CORPORATION, Kariya, Aichi-pref. (JP)

(72) Inventors: Kazutoshi Kodama, Kariya (JP); Hirofumi Noda, Kariya (JP)

(73) Assignee: DENSO CORPORATION, Kariya (JP)

( * ) Notice: Subject to any disclaimer, the term of this patent is extended or adjusted under 35 U.S.C. 154(b) by 798 days.

(21) Appl. No.: 14/945,742

(22) Filed: Nov. 19, 2015

(65) Prior Publication Data

US 2016/0146768 A1 May 26, 2016

(30) Foreign Application Priority Data

Nov. 20, 2014 (JP) ................................. 2014-235361

(51) Int. Cl.
*G01N 33/00* (2006.01)
(52) U.S. Cl.
CPC ................................ *G01N 33/0027* (2013.01)
(58) Field of Classification Search
CPC ............. G01N 33/0027; G01N 27/407; G01N 27/4077
USPC ................... 73/23.31, 23.32, 114.69–114.73, 73/31.03–31.05; 403/28–30; 204/424–431
See application file for complete search history.

(56) References Cited

U.S. PATENT DOCUMENTS

| | | | | |
|---|---|---|---|---|
| 4,425,476 A * | 1/1984 | Kyle | ................... | H01B 17/305 |
| | | | | 174/152 GM |
| 5,228,975 A * | 7/1993 | Yamada | ............... | G01N 27/407 |
| | | | | 204/421 |
| 5,739,414 A | 4/1998 | Paulus et al. | | |
| 5,886,248 A | 3/1999 | Paulus et al. | | |
| 6,223,583 B1 | 5/2001 | Friese et al. | | |
| 6,418,777 B1 | 7/2002 | Noda et al. | | |
| 6,550,309 B1 * | 4/2003 | Noda | ................... | G01N 27/407 |
| | | | | 204/424 |
| 7,341,650 B2 * | 3/2008 | Matsuo | .............. | G01N 27/4077 |
| | | | | 204/426 |
| 2003/0024300 A1 | 2/2003 | Kojima | | |

FOREIGN PATENT DOCUMENTS

| | | |
|---|---|---|
| JP | H11-513113 | 11/1999 |
| JP | 2000-509823 | 8/2000 |
| JP | 2001-208725 | 8/2001 |
| JP | 2003-043004 | 2/2003 |

* cited by examiner

*Primary Examiner* — Daniel S Larkin
(74) *Attorney, Agent, or Firm* — Nixon & Vanderhye P.C.

(57) ABSTRACT

A gas sensor is provided which includes a hollow metallic housing, a sensor device installed in the housing, and a seal disposed in the housing to hermetically isolate between the housing and the sensor device. The housing has an inner shoulder formed on an inner periphery thereof. The seal is retained on the inner shoulder. The seal is made up of a powder body and a glass body. The powder body is made of inorganic powder and mounted on the inner shoulder. The glass body is arranged on the powder body and has a varying coefficient of thermal expansion which alleviates a difference in thermal expansion between the sensor device and the housing, thereby ensuring the stability of hermetic sealing ability of the seal in high-temperature environments.

18 Claims, 7 Drawing Sheets

GAS SENSOR

CROSS REFERENCE TO RELATED DOCUMENT

The present application claims the benefit of priority of Japanese Patent Application No. 2014-235361 filed on Nov. 20, 2014, the disclosure of which is incorporated herein by reference.

BACKGROUND

1. Technical Field

This disclosure relates generally to a gas sensor equipped with a housing, a gas sensing device, and a sealing mechanism working to hermetically seal between the housing and the gas sensing device.

2. Background Art

Modern automotive vehicles use gas sensors in measuring the concentration of a given gas component contained in emissions from an internal combustion engine. The typical type of such gas sensors include a hollow metallic housing, a gas sensing device installed in the housing, and a seal which hermetically seals between the gas sensing device and the housing to block inflow of gas to be measured, such as exhaust gas, as having entered a top end portion of the gas sensing device, into a rear end portion of the gas sensing device.

Japanese Patent First Publication No. 2001-208725 teaches a gas sensor which has insulating powder disposed in a space among an outer peripheral surface of a gas sensing device, a flange formed on the outer peripheral surface of the gas sensing device, and an inner peripheral surface of a housing. The gas sensor also has a retainer and a swage ring which are disposed on the insulating powder. The housing has a rear end crimped to press the insulating powder tightly through the retainer and the swage ring to create an air-tight seal.

The above structure, however, needs lots of parts for ensuring the air-tight seal, thus resulting in a complicated process of assembling such parts. This also leads to an increase in production cost of the gas sensor. Due to the occurrence of creeping of the housing or in terms of a service temperature limit of talc, there is a possibility that the air-tight seal may deteriorate in high-temperature environments, for example, at 750° C. or more.

SUMMARY

It is therefore an object of this disclosure to provide an improved structure of gas sensor which is allowed to be produced at a decreased cost and designed to have a hermetic seal resistant to high temperatures.

According to one aspect of the invention, there is provided a gas sensor which comprises: (a) a metallic housing which has a given length with a front end and a rear end, the housing also having a hole formed therein; (b) an inner shoulder formed on an inner periphery of the housing to define a rear hole portion of the hole of the housing, the rear hole portion being closer to the rear end of the housing than the inner shoulder is; (c) a sensor device which is disposed in the hole of the housing and includes a gas sensing device with a ceramic outer surface or an assembly of a ceramic body and the gas sensing device inserted into the ceramic body; and (d) a seal which hermetically seals between the sensor device and the housing.

The seal is disposed in the rear hole portion of the housing and includes a powder body and a glass body. The powder body is made of inorganic powder and mounted on the inner shoulder within the rear hole portion. The glass body is arranged on the powder body and has a graduated thermal expansion structure which alleviates a difference in thermal expansion between the sensor device and the housing.

The gas sensor has the inner shoulder formed on the inner periphery of the housing which is exposed to the hole. The seal is made up of the powder body and the glass body. The powder body is, as described above, made of inorganic powder laid on the inner shoulder within the rear hole portion. The glass body works to absorb the difference in thermal expansion between the sensor device and the housing, thus ensuring the airtightness achieved by the seal in high-temperature environments. For example, if the powder body is cracked in high-temperature environments, the glass body serves to keep the hermetic seal suitable for hermetically isolating between the sensor device and the housing. The glass body is, as described above shaped to have the graduated thermal expansion structure which works to alleviate the difference in thermal expansion between the gas sensing device and the housing. This minimizes the possibility of breakage of the glass body, thus enhancing the reliability of hermetic sealing ability of the seal.

The powder body is disposed directly on the inner shoulder of the housing. If the glass body is placed directly on the inner shoulder, it will result in a partial lack of absorbing the difference in thermal expansion between the housing and the sensor device regardless of the varying coefficient of thermal expansion of the glass body. In order to avoid this drawback, the gas sensor is engineered to have the powder body placed on the inner shoulder of the housing.

The seal is, as described above, made from glass and inorganic powder, in other words, fabricated by a decreased number of parts. The glass body serves to create hermetic seals between itself and the housing and between itself and the sensor device. This eliminates need for the swaging, as required by the conventional structure discussed in the introductory part of this application. This results in a simple production process and a decrease in production cost of the gas sensor.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Embodiments of a gas sensor 1 will be described below with reference to the drawings. In the following discussion, the head or front end of the gas sensor 1 (i.e., a lower portion of the gas sensor 1, as viewed in the drawings) is a portion of the gas sensor 1 exposed to gas to be measured (which will also be referred to as target gas below), while the base end or rear end of the gas sensor 1 is a portion of the gas sensor opposed to the front end in a lengthwise direction thereof.

The gas sensor 1 is equipped with a sensor device. The sensor device may be made either by only a gas sensing device or by an assembly of a ceramic body and the gas sensing device installed in the ceramic body.

The gas sensor 1 has a sealing mechanism equipped with a glass body. The glass body has a graduated thermal expansion structure which alleviates a difference in thermal expansion between the sensor device and a housing of the gas sensor 1. The graduated thermal expansion structure has a varying coefficient of thermal expansion. A difference between a maximum value and a minimum value of the coefficient of thermal expansion is preferably $2 \times 10^{-6}/°C$. or less in order to minimize the possibility of thermal breakage of the sealing mechanism.

The housing has a hole and an inner shoulder formed on an inner periphery or wall of the hole. The inner shoulder has an inner diameter smaller than that of a major portion of the hole. The sealing mechanism is made up of the glass body and a powder body and disposed on the inner shoulder. The inner shoulder is shaped to retain the powder body thereon.

First Embodiment

Figure 1:
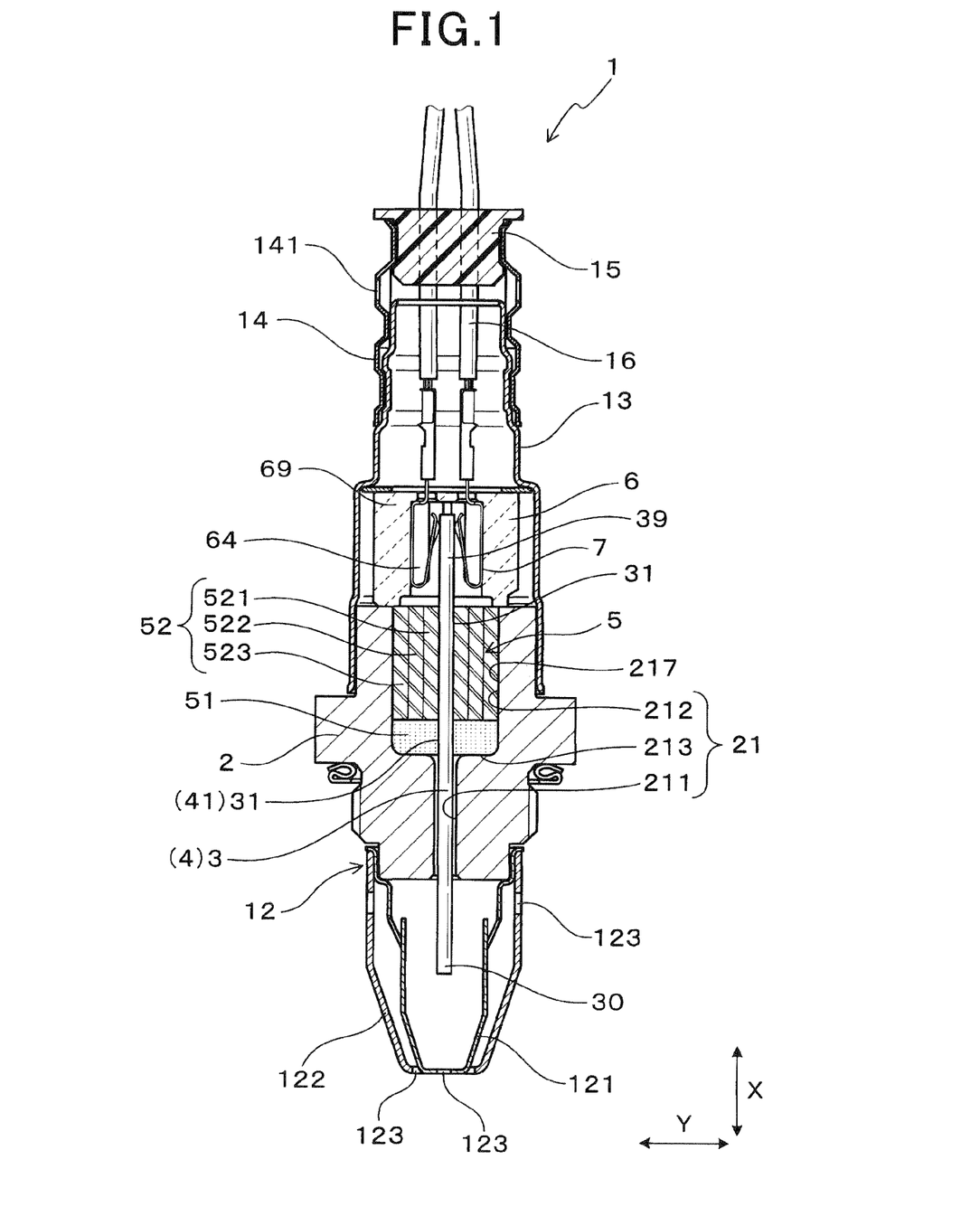
FIG. 1 is a longitudinal sectional view which illustrates a gas sensor according to an embodiment.
Figure 2:
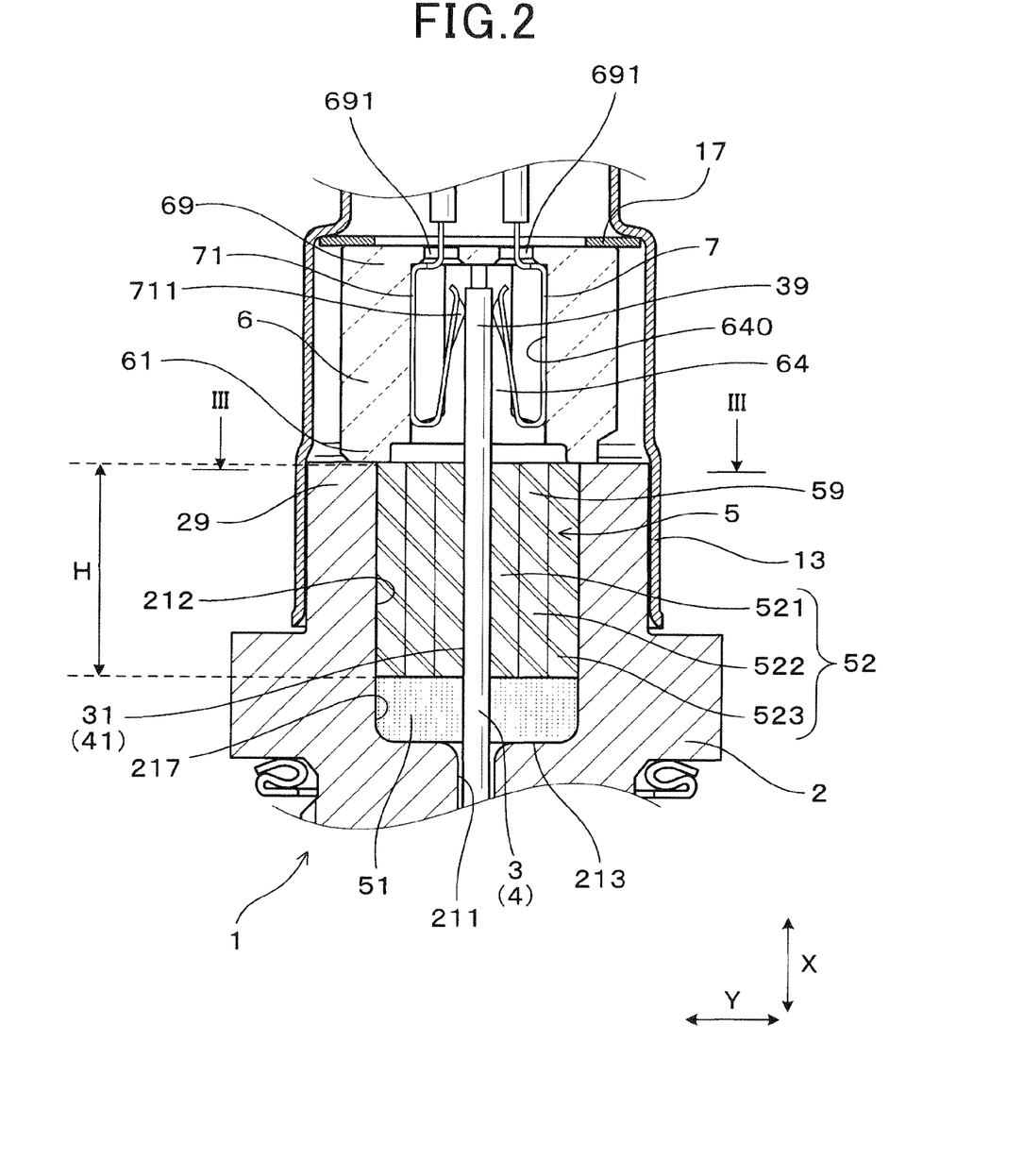
FIG. 2 is a partial longitudinal sectional view of the gas sensor of FIG. 1 which illustrates a structure of a seal installed in the gas sensor.
Figure 3:
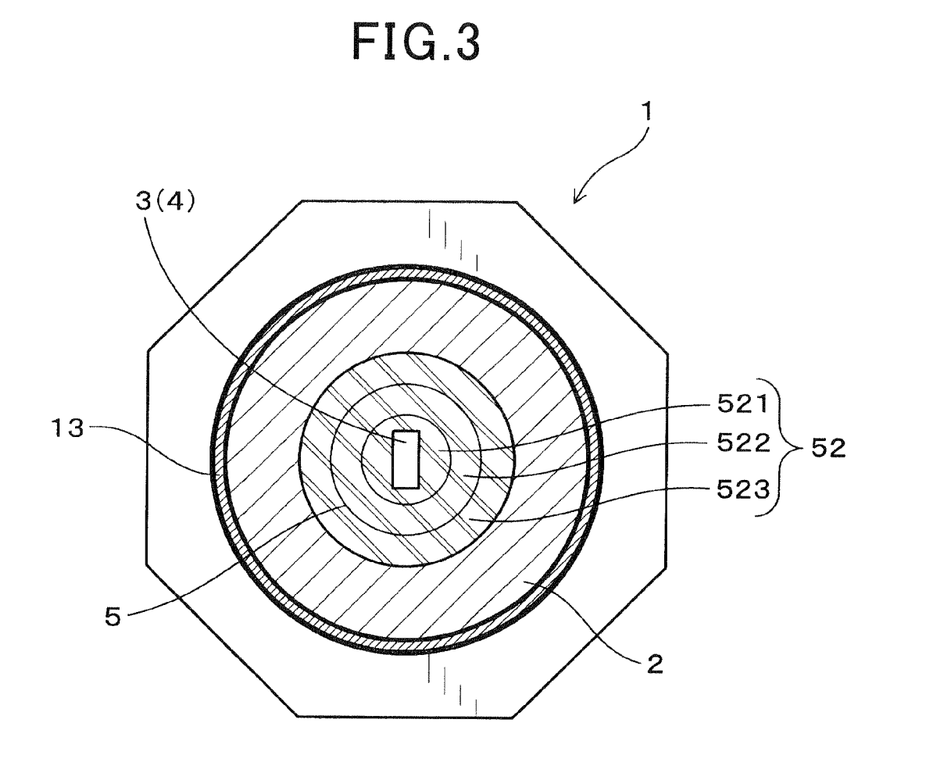
FIG. 3 is a traverse sectional view, as taken along the line III-III in FIG. 2.

Referring to FIGS. 1 to 3, includes a metallic hollow cylindrical housing 2, the sensor device 4 which is disposed inside an inner peripheral cylindrical hole 21 of the housing 2 and equipped with the gas sensing device 3, and a seal 5 which hermetically isolate between the sensor device 4 and the housing 2. The housing 2 has a given length with a front end closer to the front end of the gas sensor 1 and a rear end closer to the rear end of the gas sensor 1. The length of the housing 2 is aligned with the length of the gas sensor 1.

The cylindrical hole 21 of the housing 2 has at least a portion smaller in inner diameter than a remaining portion thereof to define an inner shoulder 213 extending substantially perpendicular to the length of the gas sensor 1, in other words, to the inner periphery of the cylindrical hole 21 of the housing 2. Specifically, the cylindrical hole 21 has a given length including a front hole portion 211 located at the front side thereof (i.e., closer to the front end of the housing 2), a rear hole portion 212 located at the rear side thereof (i.e., closer to the rear end of the housing 2), and the inner shoulder 213 located at a boundary between the front hole portion 211 and the rear hole portion 212. In other words, the inner shoulder 213 defines the rear hole portion 212 closer to the rear end of the housing 2 than the inner shoulder 213 is.

The rear hole portion 212 is greater in diameter than the front hole portion 211. In other words, the inner diameter of a front portion of the cylindrical hole 21 is smaller than that of a rear portion of the cylindrical hole 21. The seal 5 is disposed inside the rear hole portion 212. The seal 5 includes a powder body 51 and a glass body 52. The powder body 51 is made of inorganic powder disposed on the inner shoulder 213 within the rear hole portion 212. The glass body 52 is placed on the powder body 51 within the rear hole portion 212. The glass body 52 is designed to have a graduated thermal expansion structure which alleviates a difference in thermal expansion between the sensor device 4 and the housing 2, which will be discussed below in detail.

The front or front end side, as referred to herein, is one of ends of the length of the gas sensor 1 in an X-direction, as illustrated in FIGS. 1 and 2, which is exposed to the target gas, while the rear or rear end side is the other end of the gas sensor 1. In use, the gas sensor 1 is installed in an exhaust pipe of an automotive vehicle to measure the concentration of, for example, oxygen ($O_2$) contained in exhaust emissions flowing through the exhaust pipe. A direction perpendicular to the X-direction will also be referred to as a radial direction Y of the gas sensor 1.

The gas sensing device 3, as illustrated in FIGS. 1 to 3, works to measure the concentration of a given component of gas (i.e., the target gas). In this embodiment, the sensor device 4 is made only of the gas sensing device 3. The gas sensing device 3 is of a planar shape made up of a laminate of ceramic and electrode layers (not shown). The gas sensing device 3 has electrodes (not shown) formed on the outer surface of an end thereof in an axial direction X of the gas sensor 1 (i.e., a lengthwise direction of the housing 2 or the sensor device 4), but most of the outer surface of the gas sensing device 3 is made of alumina (i.e., ceramics). Specifically, at least a portion of the outer surface of the gas sensing device 3 which is hermetically covered with the seal 5 within the rear hole portion 212 is made of alumina.

The housing 2 is of a hollow cylindrical shape and made of SUS430. The cylindrical hole 21 of the housing 2 includes the front hole portion 211 and the rear hole portion 212 which is greater in inner diameter than the front hole portion 211. The gas sensing device 3 is disposed in the front hole portion 211 and the rear hole portion 212 which are aligned and communicate with each other. The inner shoulder 213 is, as already discussed in FIGS. 1 and 2, formed at the boundary between the rear hole portion 212 and the front hole portion 211. The inner shoulder 213 extends horizontally, that is, perpendicular to the length of the gas sensor 1 (i.e., the gas sensing device 3). In other words, the inner shoulder 213 extends parallel to the radial direction Y of the gas sensor 1, but however, may be inclined at a given angle to the length of the gas sensor 1 (i.e., to the inner periphery of the housing 2).

A space above the inner shoulder 213 within the rear hole portion 212 is filled with inorganic powder to form the powder body 51. Specifically, a space surrounded by the outer side surface 31 of the gas sensing device 3 (i.e., the outer peripheral surface 41 of the sensor device 4), the inner shoulder 213 of the housing 2, the inner peripheral surface 217 of the housing 2, and the glass body 52 is occupied by the powder body 51. The glass body 52 does not contact the inner shoulder 213. The inorganic powder of the powder body 52 is talc.

The glass body 52 is adhered to the outer side surface 31 of the gas sensing device 3 and the inner peripheral surface 217 of the rear hole portion 212. In other words, the outer side surface 31 of the gas sensing device 3 and the inner peripheral surface 217 of the housing 2 are hermetically sealed by the glass body 52 to achieve the air tight ability of the seal 5.

The glass body 52 is made up of a plurality of hollow cylindrical glass layers 521, 522, and 523 which are laid to overlap each other in the radial direction Y and different in coefficient of thermal expansion from each other. The coefficients of thermal expansion of the glass layers 521, 522, and 523 become greater stepwise outwardly in the radial direction Y of the glass body 52. In other words, the glass body 52 has a coefficient of thermal expansion which increases stepwise from the inner side to the outer side thereof in the radial direction Y. Specifically, the coefficient of thermal expansion of the glass layer 521 is $8 \times 10^{-6}/°$ C. The coefficient of thermal expansion of the glass layer 522 is $9 \times 10^{-6}/°$ C. The coefficient of thermal expansion of the glass layer 523 is $10 \times 10^{-6}/°$ C. The greatest difference among the coefficients of thermal expansion of the glass layers 521, 522, and 523 is less than or equal to $2 \times 10^{-6}/°$ C. The alumina which forms the outer surface of the gas sensing device 3 has a coefficient of thermal expansion of $7 \times 10^{-6}/°$ C. SUS430 making the housing 2 has a coefficient of thermal expansion of $12 \times 10^{-6}/°$ C. Consequently, there is no material whose coefficient of thermal expansion is higher or lower than those of the gas sensing device 3, the glass body 52, and the housing 2 by more than $2 \times 10^{-6}/°$ C. among the gas sensing device 3, the glass body 52, and the housing 2.

The double-walled front cover assembly 12 made up of an inner cover 121 and an outer cover 122 is, as illustrated in FIG. 1, secured to the front or head of the housing 2. The inner cover 121 is disposed inside the outer cover 122 to surround the front portion 30 of the gas sensing device 3. The inner cover 121 and the outer cover 122 of the front cover assembly 12 have gas holes 123 through which the target gas is admitted into or discharged outside the front cover assembly 12.

The gas sensor 1 also includes a first rear cover 13 and a second rear cover 14. The first rear cover 13 is secured to the rear end of the housing 2 to cover the rear end portion 39 of the gas sensing device 3. The second rear cover 14 is fixed on the rear of the first rear cover 13. The second rear cover 14 has formed therein air inlet holes 141 through which fresh air is admitted into the gas sensor 1. The second rear cover 14 has a rear end opening closed by a sealing member 15 such as rubber bush. The sealing member 15 has formed therein four holes through which four leads 16 pass. The leads 16 are connected to an external device.

The porcelain insulator 6 is, as illustrated in FIGS. 1 and 2, installed on the rear end of the seal 5 within the first rear cover 13. The porcelain insulator 6 covers the rear end portion 39 of the gas sensing device 3. The porcelain insulator 6 has formed therein an inner chamber 64 in which the rear end portion 39 of the gas sensing device 3 is disposed. The gas sensor 1 is also equipped with contact members 7 which are retained by the porcelain insulator 6 to hold the gas sensing device 3. The contact members 7 are placed in electrical contact with electrode terminals (not shown) disposed on the gas sensing device 3. The porcelain insulator 6, as can be seen in FIG. 2, has formed in the rear end portion 69 four through holes 691 through which portions of the contact members 5 pass. The holes 691 extend in the axial direction X and communicate with the inner chamber 64 of the porcelain insulator 6.

The four contact members 7 are, as clearly illustrated in FIG. 2, retained within the inner chamber 64 of the porcelain insulator 6. Each of the contact members 7 is implemented by a spring terminal 71 formed by bending a metallic plate. Each of the spring terminals 71 is electrically connected to one of the leads 16 and inserted into one of the through holes 691 of the porcelain insulator 6. Each of the spring terminals 71 is held by the peripheral wall 640 of the inner chamber 64. Each of the spring terminals 71 is curved or bent inwardly and disposed in the inner chamber 64. Specifically, each of the spring terminals 71 is made of a U-shaped plate made up of an outer strip and an inner strip. The inner strip of each of the spring terminals 71 has a contact 711 which inwardly bulges to make an electric contact with one of the electrode terminals (not shown) of the gas sensing device 3.

The rear end 59 of the seal 5 and the rear end 29 of the housing 2 are, as clearly illustrated in FIG. 2, placed in direct contact with the front end 61 of the porcelain insulator 6.

An annular disc spring 17 is, as illustrated in FIG. 2, disposed between the rear end 69 of the porcelain insulator 6 and the first rear cover 13. The porcelain insulator 6 is urged elastically by the disc spring 17 toward the front side of the gas sensor 1, that is, toward the seal 5 and the housing 2, so that it is kept from being moved in the axial direction X.

How to form or fabricate the seal 5 in the gas sensor 1 will be described below.

First, the gas sensing device 3 is inserted into the cylindrical hole 21 of the housing 2. Next, inorganic powder (i.e., talc) is put on the inner shoulder 213 within the rear hole portion 212. Three different kinds of glass cylinders (will also be referred to as glass compacts below) A, B, and C whose coefficient of thermal expansion are different from each other are prepared. The glass cylinder A is used to form the glass layer 521, as described above, and has a controlled coefficient of thermal expansion which will be that of the glass layer 521. The glass cylinder A is of a hollow cylinder with a center hole through which the gas sensing device 3 is to be inserted. The glass cylinder B is used to form the glass layer 522 and has a controlled coefficient of thermal expansion which will be that of the glass layer 522. The glass cylinder B is of a hollow cylinder with a center hole in which the glass cylinder A is to be disposed. The glass cylinder C is used to form the glass layer 523 and has a controlled coefficient of thermal expansion which will be that of the glass layer 523. The glass cylinder C is of a hollow cylinder with a center hole in which the glass cylinder B is to be disposed. The glass cylinder A is first put on the gas sensing device 3. The glass cylinders B and C are then fabricated on the glass cylinder A, respectively. The assembly of the glass cylinders A, B, and C is disposed on the inorganic powder within the rear hole portion 212.

Subsequently, the assembly of the glass cylinders A, B, and C and the inorganic powder are fired to complete the seal 5. Specifically, the firing is performed by increasing the glass cylinders A, B, and C and the inorganic powder up to 850° C. at a rate of 10° C./minute, kept it for 60 minutes, and then cooling it at a rate of −5° C./minute for 170 minutes. In the case where the seal 5 is, like in this embodiment, made of a plurality of glass layers, inorganic powder is preferably blended into at least one of the glass layers (i.e., the glass layer 522 in this embodiment) which is interposed between adjacent two of the glass layers in order to avoid mixing of the glass layers with each other to obstruct formation of the above described graduated thermal expansion structure.

The gas sensor 1 of this embodiment offers the following beneficial advantages.

The gas sensor 1 has the inner shoulder formed on the inner surface of the housing 2 which is exposed to the cylindrical hole 21. The seal 5 is made up of the powder body 51 and the glass body 52. The powder body 51 is made of inorganic powder laid on the inner shoulder 213 within the rear hole portion 212. The glass body 52 is made of a stack of the glass layers 521, 522, and 523 to ensure the airtightness achieved by the seal 5 in high-temperature environments. For example, if the powder body 51 is cracked in high-temperature environments, the glass body 52 serves to keep the hermetic seal suitable for hermetically isolating between the rear portion and front portion of the gas sensing device 3. The glass body 52 is, as described above shaped to have the graduated thermal expansion structure which works to absorb a difference in thermal expansion between the gas sensing device 3 and the housing 2. This minimizes the possibility of breakage of the glass body 52, thus enhancing the reliability of hermetic sealing ability of the seal 5.

The powder body 51 is disposed directly on the inner shoulder 213 of the housing 2. If the glass body 52 is placed directly on the inner shoulder 213, it will, as stated later in the comparative example No. 1, result in a partial lack of absorbing the difference in thermal expansion between the housing 2 and the gas sensing device 3 regardless of the change in coefficient of thermal expansion of the glass body 52 in the radial direction between the housing 2 and the gas sensing device 3. In order to avoid this drawback, the gas sensor 1 is engineered to have the powder body 51 placed directly on the inner shoulder 213 of the housing 2.

The seal 5 is, as described above, made from glass and inorganic powder, in other words, fabricated by a decreased number of parts without need for the swaging, as required by the conventional structure discussed in the introductory part of this application. This results in a simple production process and a decrease in production cost of the gas sensor 1.

The cylindrical hole 21 of the housing 2 includes the front hole portion 211, the rear hole portion 212 which is greater in diameter than the front hole portion 211, and the inner shoulder 213 formed at the boundary between the front hole portion 211 and the rear hole portion 212. This avoids the softening of the glass cylinders A, B, and C when they are being fired, so that they deform in the axial direction of the gas sensor 1 (see FIGS. 1 and 2), thus ensuring the stability in locating the seal 5 in place within the housing 2.

The glass body 52 is made up of a plurality of glass layers: the glass layers 521, 522, and 523 to have the coefficient of thermal expansion increasing stepwise outwardly in the radial direction Y, thereby facilitating the formation of the graduated thermal expansion structure of the seal 5. The glass body 52 may alternatively be formed by two or more than three glass layers as long as they serve to absorb the difference in thermal expansion between the glass body 52 and the gas sensing device 3 (i.e., the sensor device 4).

The powder body 51 is preferably made from talc as inorganic powder. This is because thermal stress arising from a difference in thermal expansion between the glass body 52 and the powder body 51 will cause the powder body 51 which is lower hardness than the glass body 52 to be broken earlier than the glass body 52, thereby minimizing the damage to the glass body 52.

The sensor device 4 of this embodiment is implemented only by the gas sensing device 3. The gas sensing device 3 is directly exposed inside the housing 2 without being covered with, for example, a ceramic body. This permits the gas sensor 1 to be reduced in dimension in the radial direction Y, which will lead to a decrease in overall size of the gas sensor 1, and also results in a decrease in number of parts making up the gas sensor 1, thus allowing the gas sensor 1 to be manufactured at a decreased cost.

The gas sensing device 3 is made of a laminate of ceramic plates, but however, may alternatively be implemented by a cup-shaped or a hollow cylindrical shaped sensing device with a bottom. It is also possible for such a structure to produce the seal 5 in the same manner as described above. The gas sensor 1 may be used as an A/F sensor or oxygen ($O_2$) sensor.

Second Embodiment

Figure 4:
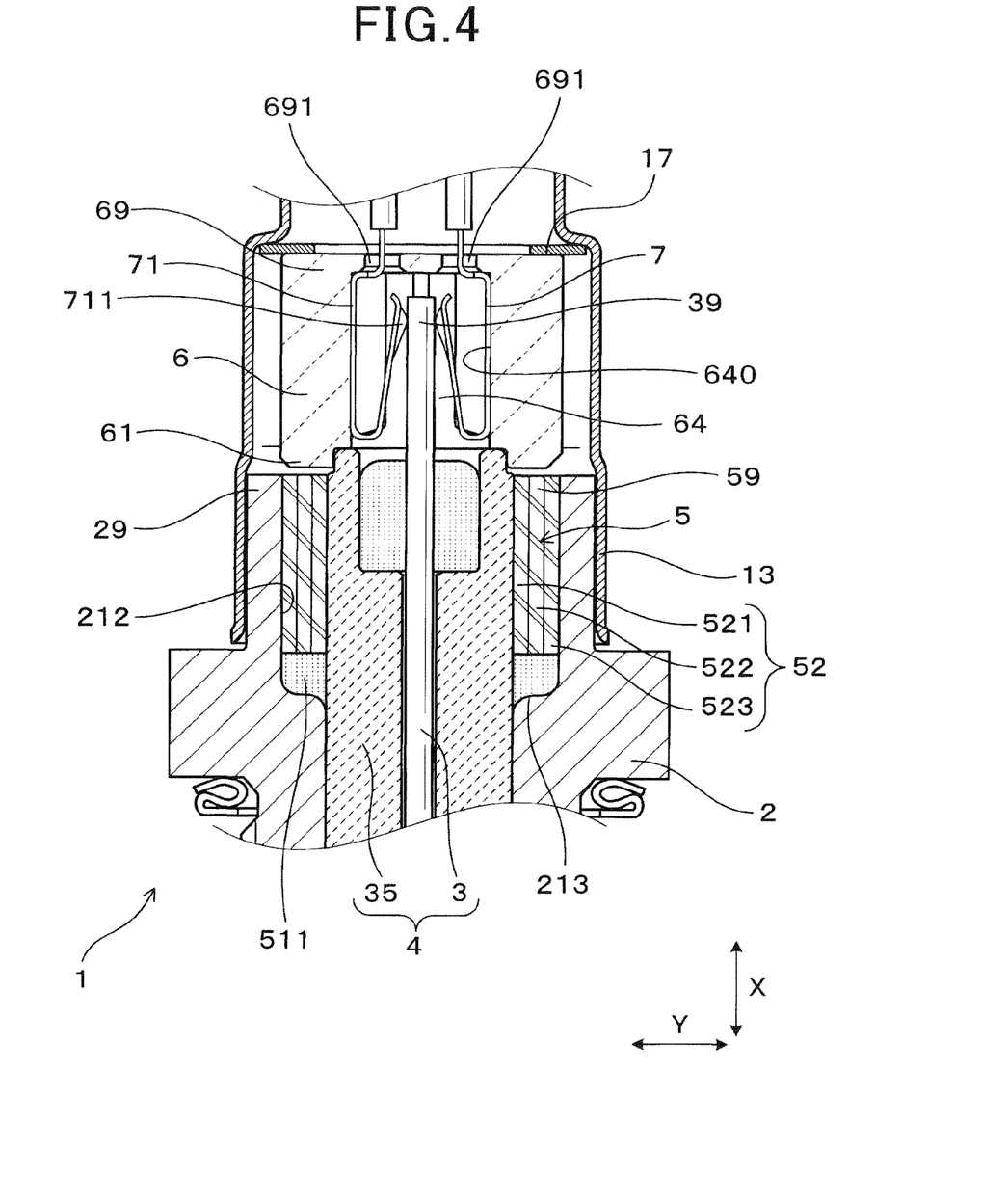
FIG. 4 is a partial longitudinal sectional view which illustrates a gas sensor equipped with a seal according to the second embodiment.

The gas sensor 1 of this embodiment is, as illustrated in FIG. 4, equipped with the sensor device 4 made up of a hollow cylindrical ceramic body 35 (which will also be referred to below as a ceramic cylinder) made of alumina and the gas sensing device 3 inserted into the ceramic cylinder 35. The gas sensing device 3 is, like in the first embodiment, made to be planar and disposed integrally in the gas sensing device 3 as a single assembly.

The planar gas sensing device 3 is installed in the ceramic cylinder 35. The ceramic cylinder 35 serves as an electric insulator to absorb thermal stress developed at corners of the gas sensing device 3. Other arrangements of the gas sensor 1 are identical with those in the first embodiment, and explanation thereof in detail will be omitted here. The same reference numbers as employed in the first embodiment refer to the same parts unless otherwise specified.

Third Embodiment

The gas sensor 1 of this embodiment is different in configuration of the housing 2 from that in the first embodiment. The gas sensor 1 is equipped with the housing 2 illustrated in FIG. 5. The housing 2 has formed on the inner periphery thereof the inner shoulder 213 exposed to the cylindrical hole 21. Specifically, the inner shoulder 213 is smaller in diameter than a major portion of the cylindrical hole 21 and defined by an inward facing protrusion formed on the inner peripheral surface 217 of the housing 2 which defines the cylindrical hole 21. The cylindrical hole 21 has a substantially constant inner diameter except the inner shoulder 213. The cylindrical hole 21 is made up of the front hole portion 211 located on the front side of the inner shoulder 213 and the rear hole portion 212 located on the rear side of the inner shoulder 213. The front hole portion 211 is identical in inner diameter with the rear hole portion 212. Other arrangements are identical with those in the first embodiment.

Figure 5:
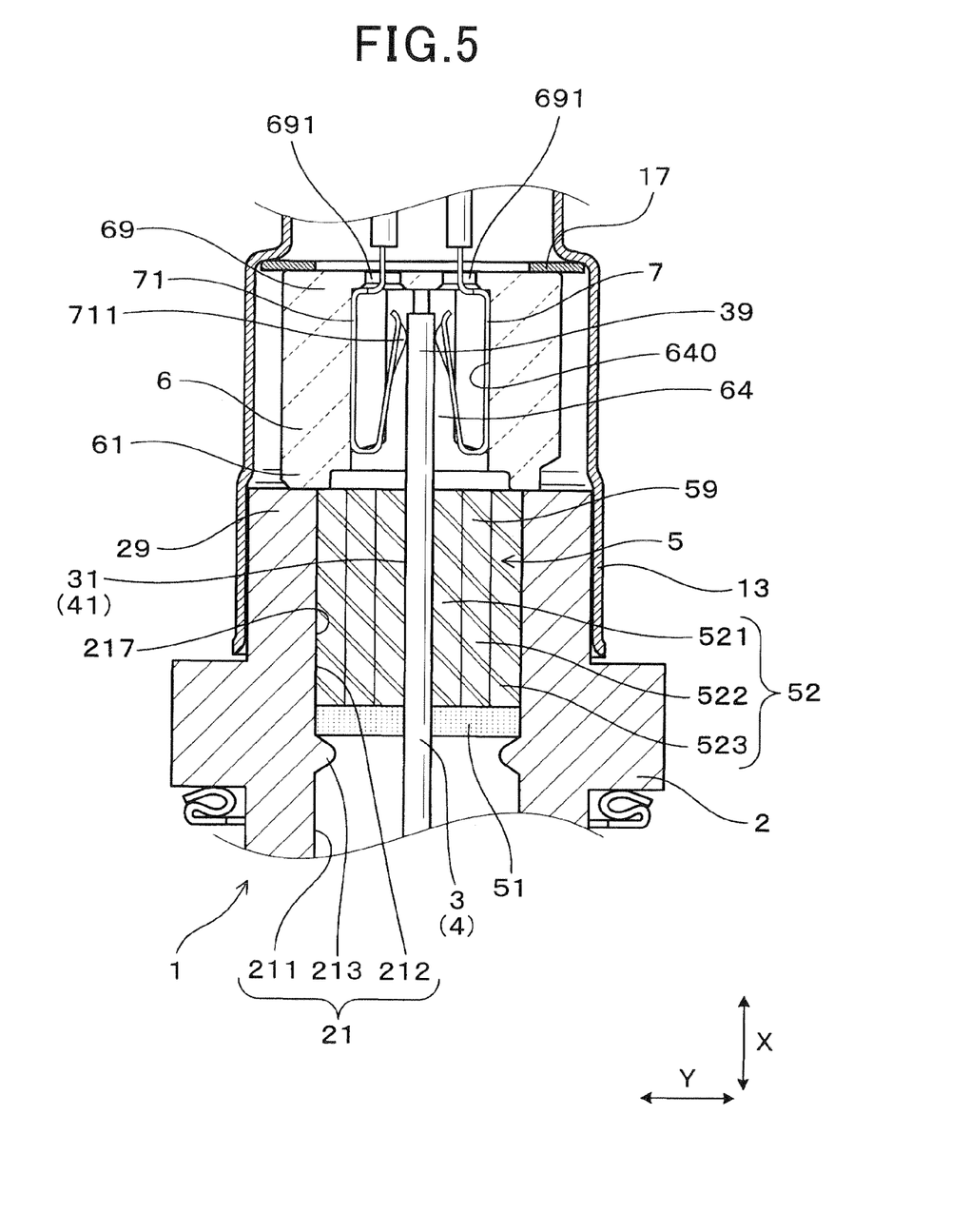
FIG. 5 is a partial longitudinal sectional view which illustrates a gas sensor equipped with a seal according to the third embodiment.

The gas sensor 1 of this embodiment, like in the above embodiments, has the glass body 52 arranged above the inner shoulder 213, thus offering the same beneficial advantages as in the first embodiment. The inner shoulder 213 is defined by an annular protrusion which is formed on the inner wall of the housing 2 and of a substantially U-shape in cross section. This results in a simple structure of the housing 2, and also results in a decrease in number of parts making up the gas sensor 1, thus allowing the gas sensor 1 to be manufactured at a decreased cost. The same reference numbers as employed in the first embodiment refer to the same parts unless otherwise specified.

Comparative Example No. 1

Figure 6:
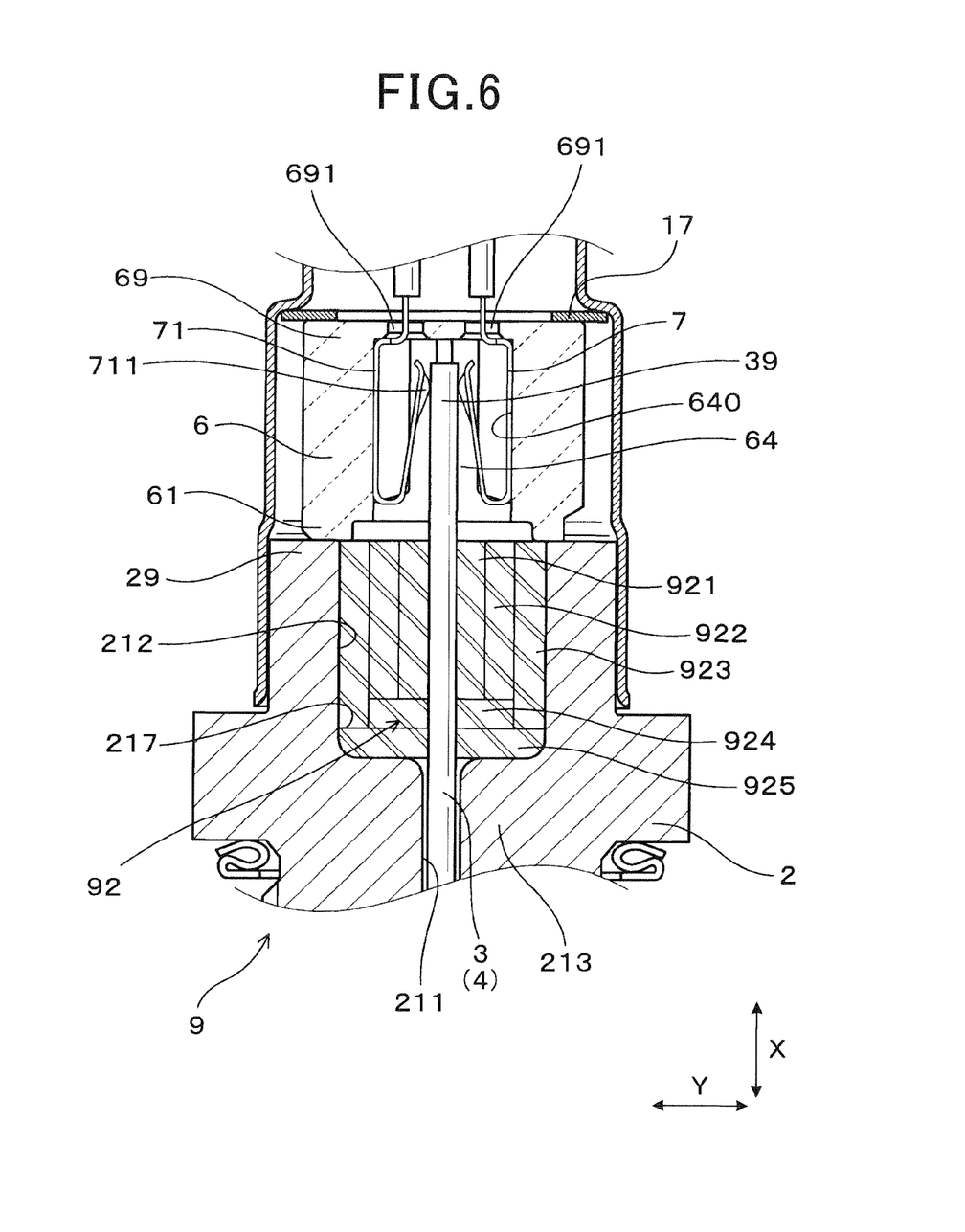
FIG. 6 is a partial longitudinal sectional view which illustrates a comparative example of a gas sensor.

FIG. 6 illustrates a gas sensor 9 as a comparative example with the gas sensor 1 in the above embodiments. The gas sensor 9 is designed not to have the powder body 51 installed in the gas sensor 1 of the first and second embodiments. Specifically, the gas sensor 9 has a seal 92 made of glass. The seal 92 is disposed on an inner shoulder of the housing 2. The seal 92 includes a plurality of hollow cylindrical glass layers 921, 922, and 923 which are laid to overlap each other in the radial direction Y. The seal 92 has a coefficient of thermal expansion increasing stepwise outwardly in the radial direction Y. The seal 92 also includes a plurality of glass layers 924 and 925 laid to overlap each other in the axial direction X. A lower one of the glass layers 924 and 925, i.e., the glass layer 925 has a coefficient of thermal expansion greater than that of the glass layer 924. A difference in coefficient of thermal expansion among the glass layers 921, 922, 923, 924, and 925 is less than or equal to $2 \times 10^{-6}/°$ C. Other arrangements of the gas sensor 9 are identical with those in the first embodiment. The same reference numbers as employed in the first embodiment refer to the same parts unless otherwise specified.

The seal 92 of this example is made up of the glass layers 921, 922, 923, 924, and 925 and does not have a block of powder such as the powder body 51 in the first and second embodiments. The seal 92, as described above, has portions whose coefficients of thermal expansion are different from each other, but will have a portion which does not absorb a difference in thermal expansion between the housing 2 and the gas sensing device 3. In the structure of the gas sensor 9 in FIG. 6, the coefficient of thermal expansion between the gas sensing device 3 and the glass layer 924 or 925 will be great. This may result in cracking which leads to deterioration of the hermetic sealing ability of the seal 92.

Fourth Embodiment

This embodiment is an example of clarifying a relation between the height of the glass body 52 and the thermal stress in the gas sensor 1 which is identical in structure with that in the first embodiment. We searched the degree of thermal stress acting on the glass body 52 for different values of the height H illustrated in FIG. 2, in other words, the length of the glass body 52 in the axial direction X. The degree of thermal stress, as referred to herein, is a maximum stress when the temperature of the glass body 52 is changed from 850° C. to 25° C. Results of the search are demonstrated in a graph of FIG. 7.

Figure 7:
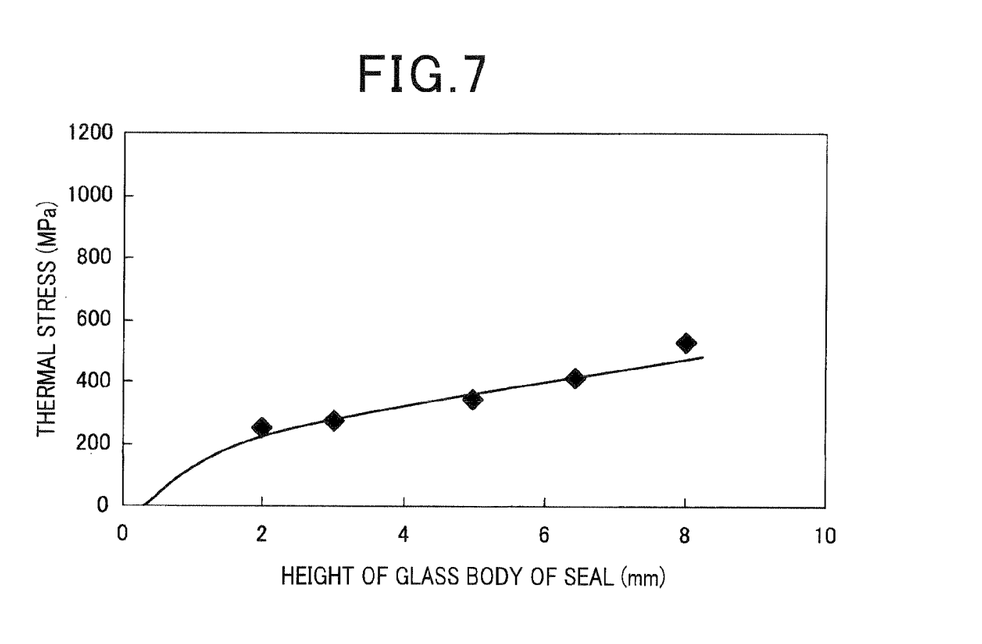
FIG. 7 is a graph which demonstrates a relation between the length of a glass body and thermal stress generated in a gas sensor according to the fourth embodiment.

The graph of FIG. 7 shows that a decrease in height H of the glass body 52 will result in a decrease in degree of stress exerted on the glass body 52. It is advisable that the height H of the glass body 52 be 8 mm or less, preferably 6 mm or less, more preferably 5 mm or less for minimizing the possibility of breakage of the glass body 52. In order to enhance the hermetic sealing ability of the glass body 52 or ensure the resistance of the glass body 52 to mechanical vibration as well as of the powder body 51, it is advisable that the height H of the glass body 52 be 1 mm or more, preferably 1.5 mm or more, more preferably 2.0 mm or more.

What is claimed is:

1. A gas sensor comprising:
    a metallic housing which has a given length with a front end and a rear end, the housing also having a hole formed therein;
    an inner shoulder formed on an inner periphery of the housing to define a rear hole portion of the hole of the housing, the rear hole portion being closer to the rear end of the housing than the inner shoulder is;
    a sensor device which is disposed in the hole of the housing and includes a gas sensing device with a ceramic outer surface or an assembly of a ceramic body and the gas sensing device inserted into the ceramic body; and
    a seal which hermetically seals between the sensor device and the housing, the seal being disposed in the rear hole portion of the housing and including a powder body and a glass body, the powder body being made of inorganic powder and mounted on the inner shoulder within the rear hole portion, the glass body being arranged on the powder body and having a graduated thermal expansion structure which alleviates a difference in thermal expansion between the sensor device and the housing.

2. A gas sensor as set forth in claim 1, wherein the hole of the housing also has a front hole portion which is closer to the front end of the housing than the rear hole portion is, the rear hole portion being greater in inner diameter than the front hole portion, and wherein the inner shoulder is located at a boundary between the front hole portion and the rear hole portion, the inner shoulder extending perpendicular or inclining to the inner periphery of the housing.

3. A gas sensor as set forth in claim 1, wherein the inner shoulder is defined by a protrusion which is formed on the inner periphery of the housing and faces inwardly within the hole of the housing.

4. A gas sensor as set forth in claim 1, wherein the glass body includes a plurality of glass layers whose coefficient of thermal expansion become greater stepwise outwardly in a radial direction of the glass body.

5. A gas sensor as set forth in claim 1, wherein the inorganic powder making the powder body is talc.

6. A gas sensor as set forth in claim 1, wherein the sensor device is made only of the gas sensing device.

7. A gas sensor as set forth in claim 1, wherein the glass body has a length in an axial direction of the gas sensor, the length being 1 to 8 mm.

8. A gas sensor as set forth in claim 1, further comprising an insulator that axially abuts a radial interface between the metallic housing and the glass body.

9. A gas sensor as set forth in claim 8, wherein the insulator comprises porcelain.

10. A gas sensor comprising:
    a metal housing which has a given length with a front end and a rear end, the housing also having a hole formed therein;
    an inner shoulder formed on an inner periphery of the housing to define a rear hole portion of the hole of the housing, the rear hole portion being closer to the rear end of the housing than the inner shoulder is;
    a sensor device which is disposed in the hole of the housing and includes a gas sensing device with a ceramic outer surface or an assembly of a ceramic body and the gas sensing device inserted into the ceramic body; and
    a seal which hermetically seals between the sensor device and the housing, the seal being disposed in the rear hole portion of the housing and including a powder body and a glass body, the powder body being made of inorganic powder and mounted on the inner shoulder within the rear hole portion, the glass body being arranged on the powder body such that the powder body is sandwiched by and between the inner shoulder and the glass body, and the glass body having a graduated thermal expansion structure which alleviates a difference in thermal expansion between the sensor device and the housing.

11. A gas sensor as set forth in claim 10, wherein the hole of the housing also has a front hole portion which is closer to the front end of the housing than the rear hole portion is, the rear hole portion being greater in inner diameter than the front hole portion, and wherein the inner shoulder is located at a boundary between the front hole portion and the rear hole portion, the inner shoulder extending perpendicular or inclining to the inner periphery of the housing.

12. A gas sensor as set forth in claim 10, wherein the inner shoulder is defined by a protrusion which is formed on the inner periphery of the housing and faces inwardly within the hole of the housing.

13. A gas sensor as set forth in claim 10, wherein the glass body includes a plurality of glass layers whose coefficient of thermal expansion become greater stepwise outwardly in a radial direction of the glass body.

14. A gas sensor as set forth in claim 10, wherein the inorganic powder making the powder body is talc.

15. A gas sensor as set forth in claim 10, wherein the sensor device is made only of the gas sensing device.

16. A gas sensor as set forth in claim 10, wherein the glass body has a length in an axial direction of the gas sensor, the length being 1 to 8 mm.

17. A gas sensor as set forth in claim 10, further comprising an insulator that axially abuts a radial interface between the metal housing and the glass body.

18. A gas sensor as set forth in claim 17, wherein the insulator comprises porcelain.

* * * * *